United States Patent [19]

Pelosi et al.

[11] 4,070,380
[45] Jan. 24, 1978

[54] 5-(4-AMIDINOPHENYL)-2-FURAMIDINE DIHYDROCHLORIDE MONOHYDRATE

[75] Inventors: Stanford S. Pelosi; Ronald E. White; George C. Wright; Chia Nien Yu, all of Norwich, N.Y.

[73] Assignee: Morton-Norwich Products, Inc., Norwich, N.Y.

[21] Appl. No.: 765,618

[22] Filed: Jan. 25, 1977

[51] Int. Cl.$^2$ ............................................ C07D 307/68
[52] U.S. Cl. .................................. 260/347.7; 424/285
[58] Field of Search ...................................... 260/347.7

[56] References Cited

U.S. PATENT DOCUMENTS 3,084,171  4/1963  Von Esch et al. ................ 260/347.7

Primary Examiner—Richard L. Raymond
Attorney, Agent, or Firm—Anthony J. Franze

[57] ABSTRACT 5-(4-Amidinophenyl)-2-furamidine dihydrochloride monohydrate is an effective anthelmintic agent.

1 Claim, No Drawings

5-(4-AMIDINOPHENYL)-2-FURAMIDINE DIHYDROCHLORIDE MONOHYDRATE

This invention relates to the compound 5-(4-amidinophenyl)-2-furamidine dihydrochloride monohydrate of the formula:

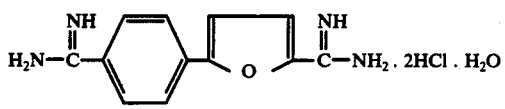

and a method for its preparation.

The compound of this invention is distinguished by its ability to combat helminth infection. When administered by gavage as a suspension in aqueous solution to mice harboring *Ascaris suum worms*, this compound accomplished a 67% reduction of the worm burden at a dose of 100 mg/kg. The compound of this invention can be combined in obvious forms such as suspensions and dispersions to provide conveniently administered dosage compositions.

The compound of this invention is readily prepared. Currently it is preferred to prepare this compound according to the following scheme:

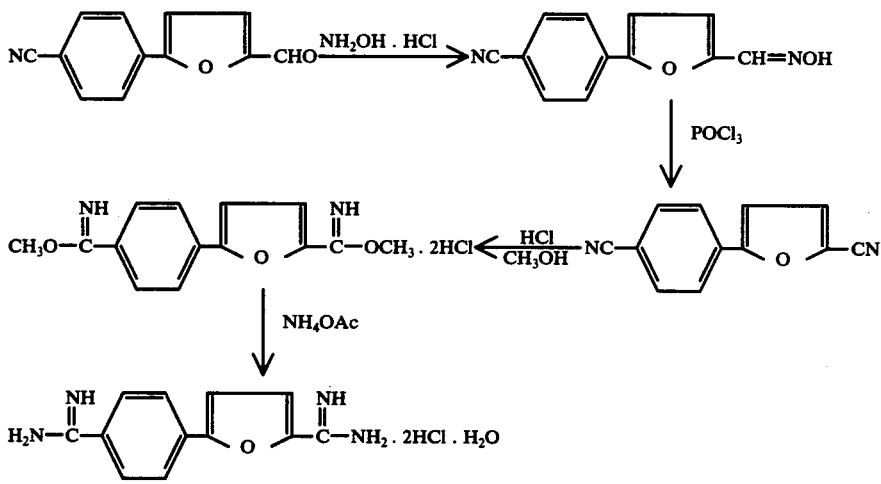

In order that this invention may be fully available to and understood by those skilled in the art, the method now preferred for making it is described.

A solution of hydroxylamine hydrochloride (5.5 g, 0.08 mole) in $H_2O$ (15 ml) was added to a solution of 5-(4-cyanophenyl)-2-furaldehyde (16 g, 0.08 mole) in ethanol (100 ml) and stirred for 1 hour at room temperature. The mixture was cooled overnight and the solid was collected by filtration to yield 16 g (94%) of oxime.

A stirred mixture of 5-(4-cyanophenyl)-2-furaldehyde oxime (16 g, 0.075 mole) and benzene (400 ml) was heated to reflux and a solution of $POCl_3$ (4 ml) in benzene (20 ml) was added dropwise over 15 minutes. The mixture was refluxed for 1½ hours and filtered while hot. The filtrate was washed with 5% $NaHCO_3$ (500 ml), $H_2O$ (500 ml), dried over $MgSO_4$ and Darco and filtered. The filtrate was stripped of solvent under reduced pressure to yield 10 g (69%) of 5-(4-cyanophenyl)-2-furonitrile.

Dry HCl was passed into a solution of 5-(4-cyanophenyl)-2-furonitrile (10 g, 0.052 mole) in absolute methanol (100 ml) with stirring at 10°–15° for 3 hours until saturated. The product was collected by filtration; yield: 12 g (71%). A mixture of methyl 5-(4-[imino(methoxy)methyl]phenyl)-2-furimidate dihydrochloride (12 g, 0.036 mole), ammonium acetate (140 g) and absolute alcohol (550 ml) was refluxed for 6 hours and stored overnight at room temperature. The mixture was poured onto ice, adjusted to pH 8 with $NH_4OH$ and the solution concentrated to one half its volume. More $H_2O$ (800 ml) was added and the product was collected by filtration. After air drying, the product was dissolved in isopropanol, adjusted to pH 3 with ethanol-HCl and ether was added until cloudiness appeared. The solution was cooled and the solid was collected by filtration to yield 9 g (83%) of 5-(4-amidinophenyl)-2-furamidine dihydrochloride monohydrate, m.p. > 300°.

Anal. Calcd. for $C_{12}H_{12}N_4O \cdot 2HCl \cdot H_2O$: C, 45.15; H, 5.06; N, 17.55; $H_2O$, 5.64. Found: C, 45.11; H, 5.19; N, 17.22; $H_2O$, 5.02.

What is claimed is:

1. The compound 5-(4-amidinophenyl)-2-furamidine dihydrochloride monohydrate.

* * * * *